United States Patent [19]

Rigney et al.

[11] Patent Number: 5,770,039
[45] Date of Patent: Jun. 23, 1998

[54] METHOD AND APPARATUS FOR MEASURING AND CONTROLLING ACTIVE OXYGEN CONCENTRATION IN A BLEACH ENVIRONMENT

[75] Inventors: Martin Peter Rigney, Roseville; Richard Jondall Mehus, Richfield; Mark Joseph Toetschinger, Crystal; John Ross Spriggs, Minneapolis, all of Minn.

[73] Assignee: Ecolab Inc., St. Paul, Minn.

[21] Appl. No.: 642,427

[22] Filed: May 3, 1996

[51] Int. Cl.⁶ .................................................. G01N 27/26
[52] U.S. Cl. ...................... 205/789; 205/792.5; 204/418; 422/82.03
[58] Field of Search ................................ 204/415, 252, 204/408, 418; 205/789, 787.5, 792.5, 793, 782.5, 782; 422/82.03

[56] References Cited

U.S. PATENT DOCUMENTS

| | | | |
|---|---|---|---|
| 3,510,421 | 5/1970 | Gealt | 204/195 |
| 3,577,332 | 5/1971 | Porter et al. | 204/195 |
| 3,887,194 | 6/1975 | Porter et al. | 277/1 |
| 3,929,603 | 12/1975 | Porter | 204/195 |
| 4,176,031 | 11/1979 | Rosenblum | 204/408 |
| 4,187,162 | 2/1980 | Dageforde | 204/195 |
| 4,874,498 | 10/1989 | Freal-Saison | 204/400 |
| 5,346,605 | 9/1994 | Wolcott et al. | 204/415 |
| 5,503,720 | 4/1996 | Teske | 204/415 |

FOREIGN PATENT DOCUMENTS 39 16910 A1  11/1990  Germany .

OTHER PUBLICATIONS

Journal Of American Waterworks Association: Johnson et al, "Chlorine Residual Measurement Cel: The HOC1 Membrane Electrode", Jun. 1978, pp. 341–348.

Scientific Encyclopedia: Norstrand 6th Ed., pp. 131–132, 2271–2272.

Rosemount Analytical: Instruction Manual: Model 450 Free Residual Chlorine Sensor Assembly, Apr. 1, 1989.

*Primary Examiner*—Bruce F. Bell
*Attorney, Agent, or Firm*—Merchant, Gould, Smith, Edell, Welter & Schmidt, P.A.

[57] ABSTRACT

The present invention provides an arrangement of equipment and an overall process for the measurement and control of active bleach concentration in a bleach environment of an industrial laundry or cleaning system. As a preferred embodiment the primary piece of equipment which renders the overall system especially useful in controlling, for example, hypochlorite ion in a bleach environment is a membrane-shielded amperometric probe. The probe is designed and membrane selected to be highly selective to fluctuations in hypochlorite ion concentration.

22 Claims, 5 Drawing Sheets

METHOD AND APPARATUS FOR MEASURING AND CONTROLLING ACTIVE OXYGEN CONCENTRATION IN A BLEACH ENVIRONMENT

BACKGROUND OF THE INVENTION

1. Field of the Invention

The present invention relates to a method and apparatus for the real time measurement and control of hypochlorite ion concentration in a bleach environment. An amperometric probe having a hydrophilic alkali-resistant membrane is utilized. The probe exhibits high sensitivity and selective, proportional (linear) response to fluctuations in hypochlorite ion concentration. The probe is also useful to determine active oxygen concentration in a peroxide media containing, for example, peracetic acid and hydrogen peroxide.

2. Description of the Prior Art

Many types of industrial laundry systems are known. These include both batch systems and continuous systems, such as tunnel washer systems. As those skilled in the art will appreciate, laundry is advanced in a tunnel washer through various cleaning stages by an auger-type mechanism. Within each stage of the washer, the environment is preferably maintained relatively constant.

Generally, within the foregoing types of industrial laundry systems, a portion of the cleaning and disinfecting is accomplished by using a bleach environment in which the pH is held at about 10 or greater. At these pH levels, equilibrium dictates that the bleach species present is nearly 100% bleaching agent, e.g. hypochlorite ion (OCl$^-$).

Within a tunnel washer (or other industrial cleaning system) the cleaning stage which includes a bleach environment should optimally be kept at a constant concentration of hypochlorite ion. The optimum concentration of hypochlorite ion provides the most favorable laundering results while minimizing excess chemical usage and fabric damage. An additional advantage of optimizing chemical usage is found in the reduced discharge of chlorine-containing species to the environment and the treatment cost when disposing of the same.

The optimization of chemical usage, however, requires a real-time, highly sensitive measurement of hypochlorite ion concentration in order to establish and maintain a predetermined (or "set") bleach concentration. When the concentration of hypochlorite ion drops below a set optimized point, then insufficient or inefficient bleaching may result. Alternatively, if the concentration of hypochlorite ion fluctuates on the high side, then the amount of fabric damage and the chemical costs may be unsatisfactorily increased. Accordingly, a measuring device is desired for accurately measuring the concentration of hypochlorite ion and providing the concentration to a control process for minimizing fluctuations.

In the past several methods have been used for measuring the concentration of oxidizing agents. For example, German Pat. DE 3926910 discloses a method of diverting a sample containing an oxidizing agent, in this case peracetic acid, followed by an automated colorometric analysis. This system, however, does not provide direct real-time measurement of oxidizing agent concentration and includes a relatively complex system incorporating pumps to sample the bleach environment and deliver reagents, along with a spectrophotometer for measurement.

Oxidation reduction potential (ORP) probes exist which have been used to measure concentrations of oxidizing agents. For example, U.S. Pat. No. 4,874,498 to Freal-Saison discloses an apparatus for regulating the concentration of an oxidizing solution, particularly a solution containing disinfecting molecules. As Freal-Saison recognized, however, use of redox potential of a disinfecting solution as a measuring parameter is only valid at constant pH. The response of the oxidation reduction potential probe varies not only with concentration but also with the pH of the environment within which the probe is inserted.

Amperometric membrane probes were originally developed with homogenous membranes and used for the determination of dissolved oxygen. The use of an amperometric probe utilizing a microporous membrane for the determination of oxidant species is generally disclosed by Johnson et al. in "Chlorine Residual Measurement Cell: The HOCl Membrane Electrode", published in the *Journal of American Waterworks Association,* June 1978, pp. 341–348. In that article, the authors disclose the use of a membrane-covered amperometric probe to measure the active disinfectant form of free chlorine (HOCl), without interference from the inactive disinfectant form (OCl$^-$). The membrane is selected for its ability to allow migration of HOCl molecules while preventing the migration of the ionic species, hypochlorite ion (OCl$^-$).

The general concept of amperometric probes and specific improvements to such general concepts are generally disclosed in several U.S. patents. For example, Dageforde, in U.S. Pat. No. 4,187,162, discloses the general concept of an amperometric probe, wherein the improvement includes utilizing a porous plug as the sole route of migration of electrolyte to the cathode area of the probe. Porter, in U.S. Pat. No. 3,929,603, discloses the general concept of an amperometric probe wherein the improvement includes pressure compensating means between the electrolyte reservoir and the environment into which the probe is inserted. Porter et al., U.S. Pat. No. 3,887,194, generally illustrates an improved method for tensioning a membrane or a film over the cathode of an amperometric measuring device.

In view of the foregoing, a need exists for a real-time measuring device or probe which is highly sensitive to concentrations of active oxygen compounds such as peroxyacids and hypochlorites in the bleach environment of a large laundry or industrial cleaning system. Preferably the measuring device and control system is one which is highly sensitive and selective, proportional (linear) to response to hypochlorite ion concentration while preventing other species from interfering with probe measurement or otherwise fouling the cathode. Furthermore, the measuring device should be incorporated into an overall arrangement of equipment or process which allows real-time feed back control of bleach addition to the large scale laundry or cleaning system in which the measuring device is used. The present invention addresses these needs as well as other problems associated with the control of hypochlorite ion concentration in large scale laundry and cleaning systems.

SUMMARY OF THE INVENTION

The present invention provides for an arrangement of equipment and an overall process for the measurement and control of active bleaching agent concentration in the bleach environment of an industrial laundry or cleaning system. A primary element which renders the overall system especially useful in controlling active oxygen concentration in a bleach environment is a membrane-shielded amperometric probe. The probe is designed, and the membrane is selected, to be highly sensitive to fluctuations in active bleaching agent concentration—while preventing other chemical species from fouling the probe or otherwise interfering with the measurement of interest. The active bleaching agent is sourced from peroxides or hypochlorites in the bleach.

Generally, the amperometric probe constructed according to the principles of the present invention comprises an electrically non-conductive body with an electrolyte reservoir therein. The probe also contains a pair of spaced electrodes. The first electrode is positioned within the electrolyte reservoir and is in contact with the electrolyte which fills the reservoir. The electrically non-conductive body includes an opening at one end to provide a passageway between the reservoir and the exterior of the body. The second electrode is mounted in the interior of the non-conductive body, but not directly within the reservoir. Instead, a porous plug is located between the reservoir and the second electrode. The second electrode is arranged and configured to lie proximate to the opening described above, and to be electrically coupled with the first electrode through the porous plug and the electrolyte. The first electrode is referred to herein as the anode while the second electrode is referred to herein as the cathode.

A hydrophilic alkali-resistant membrane overlies the cathode and is in contact with a solution containing the constituent whose concentration is to be measured. In a preferred embodiment of the present invention, the constituent to be measured is hypochlorite ion, which is the ionic form of bleach present in solutions at pH of greater than about 10. The hydrophilic alkali-resistant membrane is selected in order to provide high sensitivity to bleach concentration or fluctuations in bleach concentration at the stated pH.

Applicants have discovered that membranes selected from the group consisting of hydrophilic polysulfones, modified polysulfones, acrylics, polyamides, polyvinylidene fluorides, vinyl/acrylic copolymers or porous inorganic materials, e.g. porous alumina, have the required high sensitivity to hypochlorite ion concentration.

The sensitivity of the probe to fluctuations in active oxygen concentration is key to the economic advantages and other advantages gained from utilizing an amperometric probe based bleach addition system in industrial laundry or other cleaning systems. For example, the high sensitivity allows control of hypochlorite ion concentration at an optimum set point without concerns of dropping to a low level of hypochlorite ion concentration wherein insufficient cleaning would occur. The optimum set point also allows operation at hypochlorite ion concentrations in which no chemical is wasted as excess and laundry damage is minimized. Furthermore, disposal costs of the chlorine-containing species is reduced.

The general operation of an amperometric probe to measure ion concentration of various species has been disclosed by Gealt (U.S. Pat. No. 3,510,421); Porter et al. (U.S. Pat. No. 3,577,332); and Porter (U.S. Pat. No. 3,929,603), and the foregoing issued U.S. patents are hereby incorporated herein by reference.

The amperometric probe utilized as a sensing device in the preferred embodiment is arranged and configured with other equipment to provide for an overall system or process for controlling the concentration of hypochlorite ion in the bleach environment of industrial laundry systems (or other industrial cleaning systems) where the pH is greater than about 10. The amperometric probe produces a first electrical signal in proportion to the concentration of bleach in the bleach environment. The first electrical signal is measured by processing means which are arranged and configured to produce a second output signal which is preferably proportional relative to the measured first electrical output signal (i.e., the second output signal is preferably an amplified voltage signal). The second output signal is transmitted to an analog-to-digital converter. The resulting digital value is processed by a microprocessor and compared to a set value (i.e., a predetermined target value). In the event that the actual value is lower than the set value, then the difference between the actual and target values is provided as an error signal by the microprocessor to a means for adding bleach to the bleach environment. The bleach adding means are arranged and configured to receive the error signal and adjust the flow of bleach to the bleach environment relative to the error signal to minimize fluctuations in the concentration. Accordingly, the bleach concentration remains generally constant at a predetermined concentration. Those skilled in the art will appreciate that the system could also include means for neutralizing the bleach concentration if the actual concentration exceeded the set value.

These and various other advantages and features of the present invention are pointed out with particularity in the claims annexed hereto and forming a part hereof. However, for a better understanding of the invention, its advantages, and the objects obtained by its use, reference should be made to the drawing which forms a further part hereof, and to the accompanying descriptive matter, in which there is illustrated and described a preferred embodiment of the present invention.

BRIEF DESCRIPTION OF THE DRAWING

In the drawing, in which like reference numerals indicate corresponding parts or elements of the preferred embodiment of the present invention throughout the several views.

DETAILED DESCRIPTION OF THE PREFERRED EMBODIMENT

A detailed preferred embodiment of the present invention is disclosed herein. However, it is to be understood that the disclosed embodiment is merely exemplary of the present invention which may be embodied in various systems. Therefore, specific details disclosed herein are not to be interpreted as limiting, but rather as a basis for the claims and as a representative basis for teaching one skilled in the art to variously practice the present invention.

Probe 1

Figure 1:
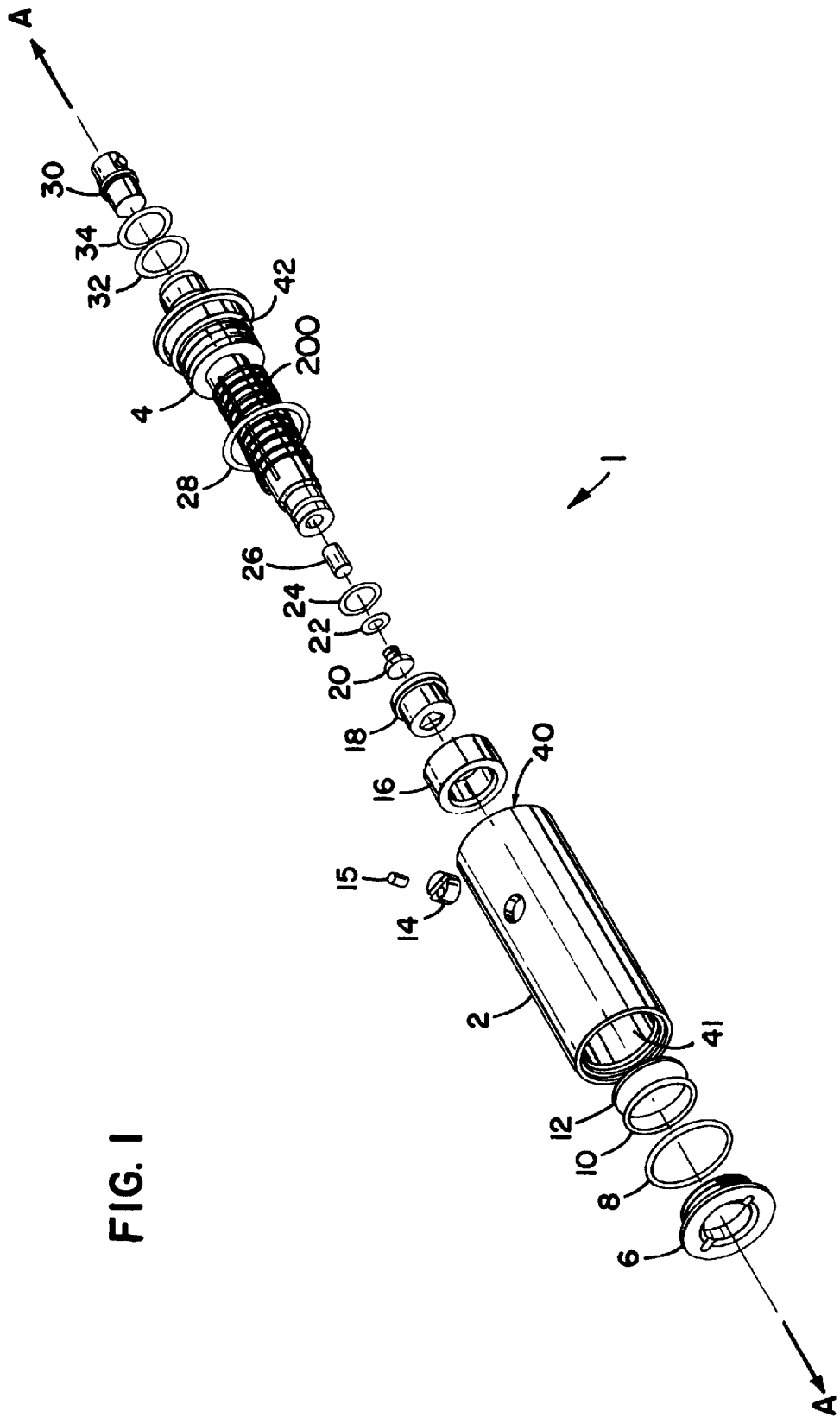
FIG. 1 is a disassembled view of an amperometric probe constructed in accordance with the principles of the present invention and depicting the assembly of the various labeled elements around a central axis labeled A—A.
Figure 2:
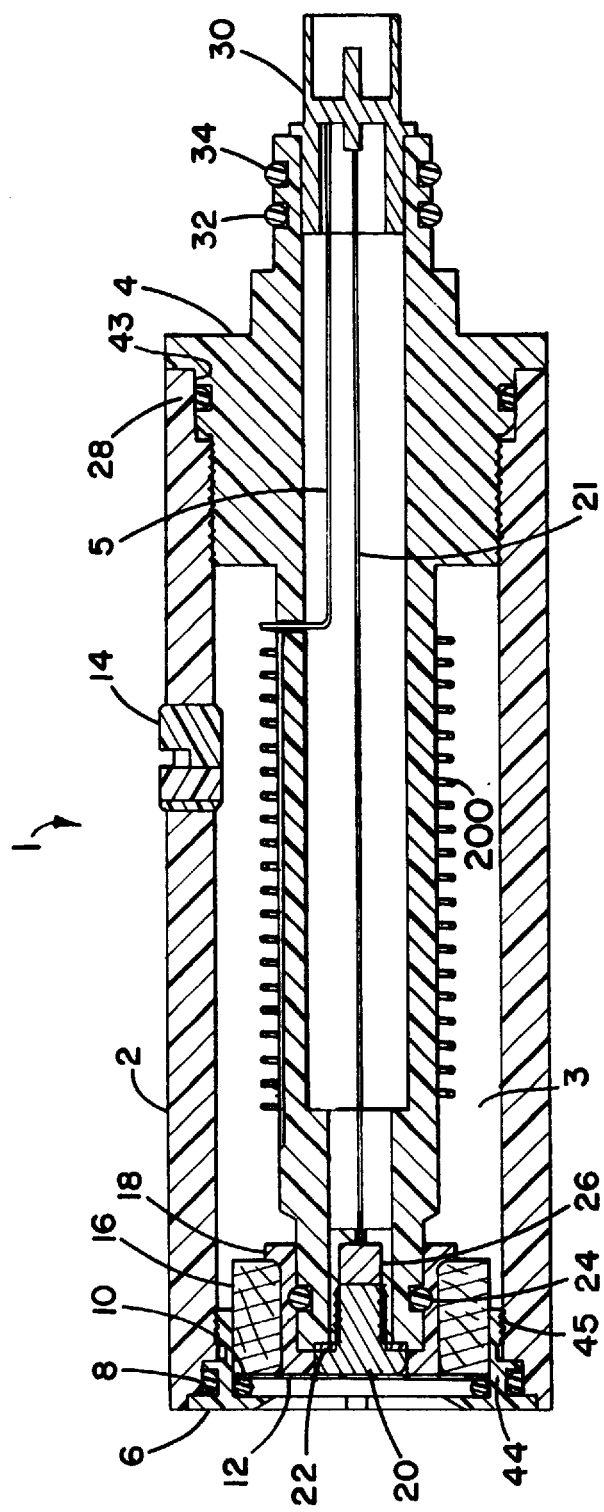
FIG. 2 represents a cross-sectional view of a preferred embodiment of an assembled amperometric probe 1 of FIG. 1.

Referring now to the drawing, FIG. 1 illustrates a disassembled view of an amperometric probe 1 which is constructed in accordance with the principles of the present invention. FIG. 2 illustrates a cross-sectional view of the amperometric probe 1 in an assembled state. As designated by line A—A in FIG. 1, the component parts of the probe 1 of the present invention are assembled about a central axis which is parallel to the longitudinal axis of the probe 1.

Still referring to FIGS. 1 and 2, the probe 1 is comprised generally of an elongated, cylindrical, electrically nonconductive body 2 which defines the outer boundaries of the electrolyte containment area 3. The opposite ends of the cylindrical electrically non-conductive body 2 define first and second circular openings 40, 41 oriented substantially perpendicular to central axis A—A.

Body shaft 4 is inserted into body 2 via first circular opening 40. Body shaft 4 threadably engages with non-conductive body 2 via threads 42 and is sealed with a first O-ring or gasket 28. When body shaft 4 is inserted into non-conductive body 2, the first O-ring 28 is compressed against an interior surface 43 of the cylindrical non-conductive body 2 in a well known manner, thereby sealing body shaft 4 and non-conductive body 2 together in a manner which prevents escape of the electrolyte.

The second opening 41 (at the opposing end of the non-conductive body 2) is enclosed by various elements comprising a membrane means. When assembled, the membrane means provide for exposure of the surface of membrane 12 to the bleach environment within which the amperometric probe 1 of the present invention is placed. In that environment, the OCl⁻ makes up the constituent of interest. The porous plug 16 restricts the flow of the electrolyte within the non-conductive body 2. The various elements enclosing the second opening 41 of the non-conductive body 2 and comprising the membrane means include a membrane cover 6 (having a sealing flange 44), a second O-ring or gasket 8, a third O-ring or gasket 10 and a membrane 12.

As shown in FIG. 2, the membrane cover 6 is an annular element which is threadably engaged to non-conductive body 2 with threads 45 located on the sealing flange 44. Preferably the membrane cover 6 and sealing flanges are constructed as a single integral piece. Second O-ring 8 is arranged and configured to reside within a groove defined within the outer circumference of the sealing flange 44. The second O-ring 8 is compressed against an interior surface of non-conductive body 2 to form a seal between the membrane cover 6 and the body 2 in a well known manner.

Third O-ring 10 is arranged and configured to reside about the inner circumference of the sealing flange 44 to provide a seal between the membrane 12 and the constituent. More specifically, the third O-ring 10 is compressed between membrane cover 6 and the outer perimeter of porous plug 16, while the membrane 12 is located between the porous plug 16 and third O-ring 10. The plug 16 is held firmly in place by body shaft 4 (discussed below), and a seal is formed about the outer perimeter of the membrane 12 and the porous plug 16. Thus, any constituent in the environment must travel through membrane 12 and cannot leak around the membrane 12.

Body shaft 4 is arranged and configured to provide mounting means for the following elements: a porous plug 16 (i.e., a porous reference junction), a cathode spacer collar 18, an O-ring or gasket 24, and a cathode 20. Body shaft 4 also aids in maintaining the proper spatial relationship of the foregoing elements to the membrane 12. Together the collar 18, the plug 16, and the cathode 20 form a generally planar surface which is parallel to membrane 12. The surface may be either just proximate to or contacting membrane 12. Preferably the resulting surface of the foregoing elements when assembled is approximately equal in diameter to the membrane 12.

The porous plug 16 has an outer diameter which fits tightly against the interior circumference of the sealing flange 44. The interior circumference may be chamfered to aid in assembling the probe 1 and guide the plug 16 into its correct position. The outer diameter of plug 16 is preferably approximately equal to the diameter of the membrane 12. Plug 16 is annular and so also defines an interior void 46. The diameter of the void is referred to herein as the interior diameter of plug 16. Cathode spacer collar 18 resides within void 46 and is arranged and configured to fit tightly against the interior diameter of the porous plug 16.

The cathode spacer collar 18 is annular and has two interior diameters which are "stepped." The first diameter is larger, is distally located from the membrane cover 6, and is generally equal to the outside diameter of the body shaft 4 at its end. The cathode spacer collar 18 is held in position by O-ring retaining means 24, which is compressed when assembled. The second diameter (located proximate to membrane cover 6) is generally equal to the outside diameter of the cathode 20. When assembled, cathode 20 resides within the second diameter of the cathode spacer collar 18. When viewed from the second opening 41, the porous plug 16, the cathode spacer collar 18 and cathode 20 resemble a "target" due to the annular nature of the plug 16 and collar 18, as well as the manner in which the elements fit with one another. The cathode spacer collar 18, in a preferred embodiment, may also be utilized to install and remove the threaded cathode 20 into the threaded cathode insert 26.

When assembled, the porous plug 16, the cathode spacer collar 18, and the cathode 20 define a planar surface generally equal in diameter to the membrane 12 and seal the electrolyte reservoir 3 from open communication between the reservoir 3 through the membrane 12 into the bleach environment outside the membrane when mounted in the bleach environment.

The porous plug 16 operates as a reference junction and is porous to the electrolyte. Dageforde, U.S. Pat. No. 4,187,162 (incorporated herein by reference) discloses use of a porous plug which is wood. However, wood degrades in high pH environments (such as the one in which probe 1 is used). Accordingly, plug 16 is preferably constructed of porous ceramic or plastic in order to establish a means for the electrolyte to communicate with the bleach environment. This is the only path of communication between the electrolyte and the bleach environment. A cathode washer 22 is provided to seal the surface between the cathode spacer collar 18, the cathode 20 and the threaded cathode insert 26.

The cathode insert 26 is manufactured from an electrically conductive material. Its interior diameter is threaded to receive the cathode 20 which includes a threaded stem to be received by the cathode insert 26. In a preferred embodiment of the present invention, the cathode 20 is manufactured from gold or is gold-plated. The electrically conductive cathode insert 26 is connected by means of a conductor 21 to an electrical terminal 30.

The anode (200) includes an electrically conductive filament or wire 5 which is wrapped around the exterior diameter of the body shaft 4 and immersed within the electrolyte 3. The anode is connected to electrical terminal 30 on the interior of body shaft 4. Electrical terminal 30 includes well-known appropriate electrical connections, not shown, for connecting the cell to an external circuit (described below). O-ring or gasket sealing devices 32 and 34 are provided on the exterior of body shaft 4 such that when terminal 30 is connected to an electrical circuit by appropriate means, the connector is protected from any deleterious environmental conditions.

A removable fill plug 14 is provided through a third opening of the exterior wall of the cylindrical electrically non-conductive body 2. This opening may be used to add electrolyte to the electrolyte reservoir 3. Provided within the fill plug 14 is a pressure-relief plug 15 which maintains the differential pressure between the bleach environment outside the amperometric probe and electrolyte solution within the probe at or near 0 (psi).

The construction of the amperometric probe 1 of the present invention, in a preferred embodiment, incorporates design features which simplify maintenance of the probe 1. The various constituent pieces of the amperometric probe 1 are threadably engaged and are sealed with O-ring type gaskets. This allows the probe 1 to be disassembled and assembled virtually without tools. Furthermore, the design of the cathode 20 in conjunction with the cathode spacer collar 18 allows installation and removal of the cathode 20 without any additional tools. The cathode spacer collar 18 is utilized as a wrench to turn the cathode 20 into the threaded interior diameter of the cathode insert 26 which is already joined to the conductor 21. Thus, the conductor path for the cathode 20 is maintained merely by threading the cathode 20 into the electrically conductive cathode insert 26. The design of the membrane cover 6 is such that the membrane 12 may be placed and held in place with proper alignment to the cathode 20 by third O-ring 10 simply by placing the membrane cover 6 in position on the body 2.

Selection of a proper membrane 12 for application in the probe 1 of the present invention is based on several criteria. Key to the selection is the permeability of the membrane 12 to the hypochlorite ion yet having chemical stability (and therefore mechanical stability) in an environment highly alkaline at pH of 10 or greater. High permeability to the hypochlorite ion is necessary to have a highly sensitive response to fluctuations in hypochlorite ion concentration within the bleach environment. The sensitivity of the probe 1 is related to the mass flux across the membrane 12 to the cathode 20.

Figure 4:
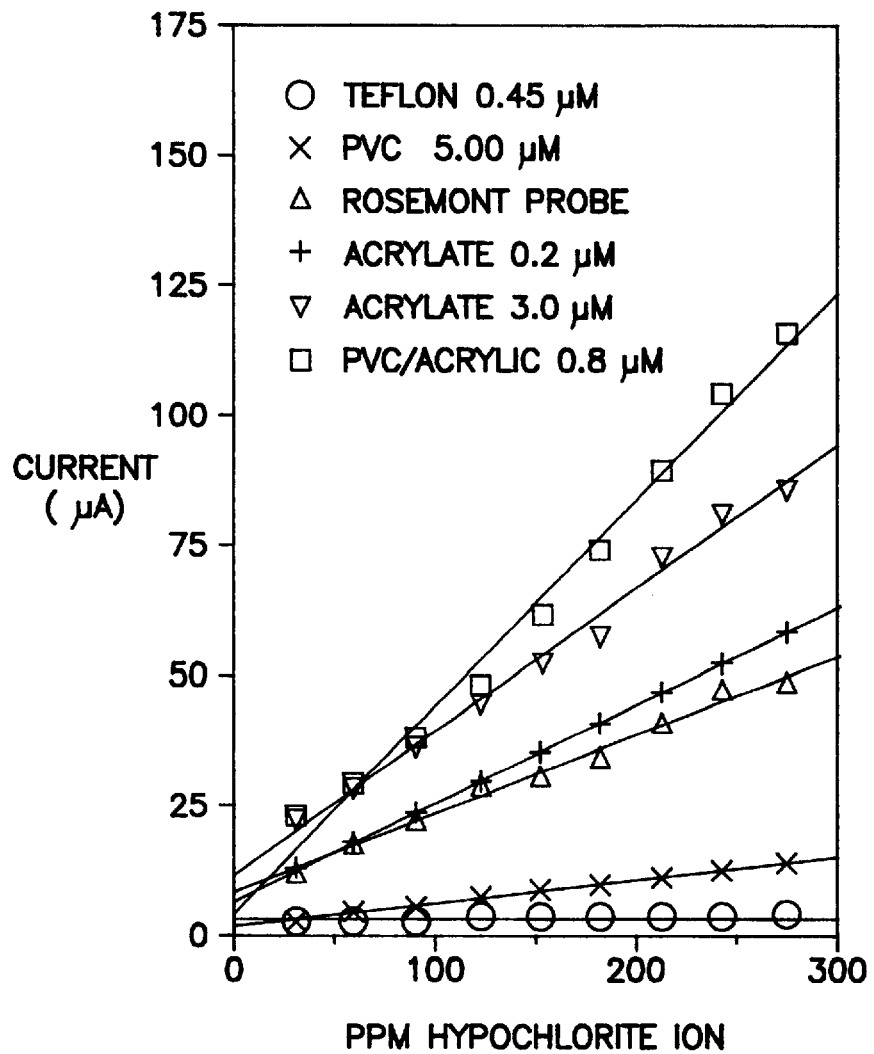
FIG. 4 is a graphical representation of experimental data depicting the current response of an amperometric probe utilizing various membrane materials at varying concentrations of hypochlorite ion.

As summarized in FIG. 4 and described in detail in Example 1 below, Applicants have discovered that certain selected membrane materials allow selective transport of hypochorite ion wherein the device is highly sensitive to fluctuations in hypochlorite ion concentration within the bleach environment. First, the membrane material must be hydrophilic in order to allow the ionic species through the pore structure of the membrane. Second, the membrane material must be mechanically stable in the highly alkaline bleach environment where pH may exceed 10. The main benefits of utilizing a hydrophilic alkaline stable membrane is to prevent fouling of the cathode by such substances as particles, soils, surfactants and other suspended solids within a cleaning system. Applicants have found that a membrane manufactured from a material of hydrophilic polysulfones, modified polysulfones, acrylics, polyamides, polyvinylidene fluorides, vinyl/acrylic copolymers or porous inorganic materials or ceramics provides the necessary selectivity for measuring flux or changes in the hypochlorite ion concentration of a bleach environment in a preferred embodiment of the amperometric probe 1.

Figure 5:
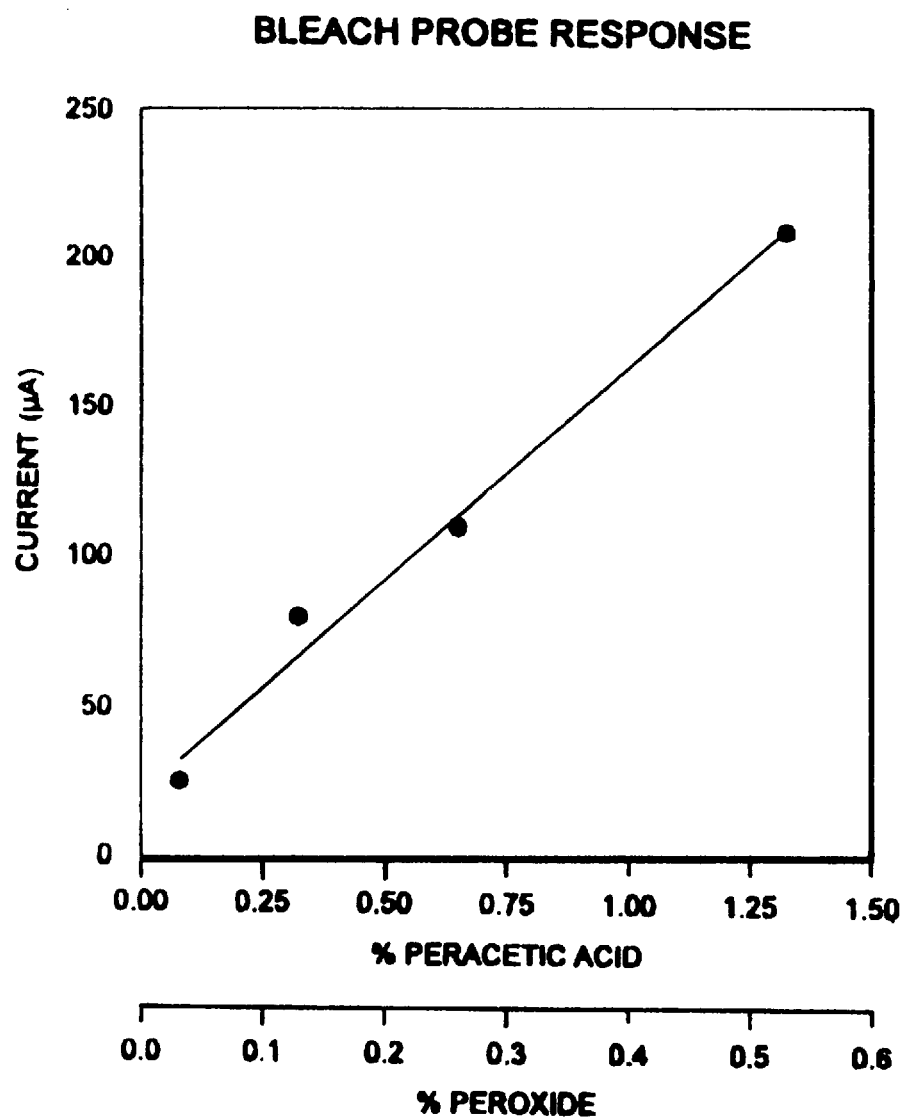
FIG. 5 is a graphical representation of experimental data depicting the current response of an amperometric probe at varying concentrations of hydrogen peroxide/peracetic acid.

FIG. 5 illustrates the applicability of the amperometric probe to peroxide/peracetic acid solutions. The graph shows the results of a study of the response of the probe to varying concentrations of a hydrogen peroxide/peracetic acid sanitizer at 0.0 V at a base gold cathode.

System 100

Figure 3:
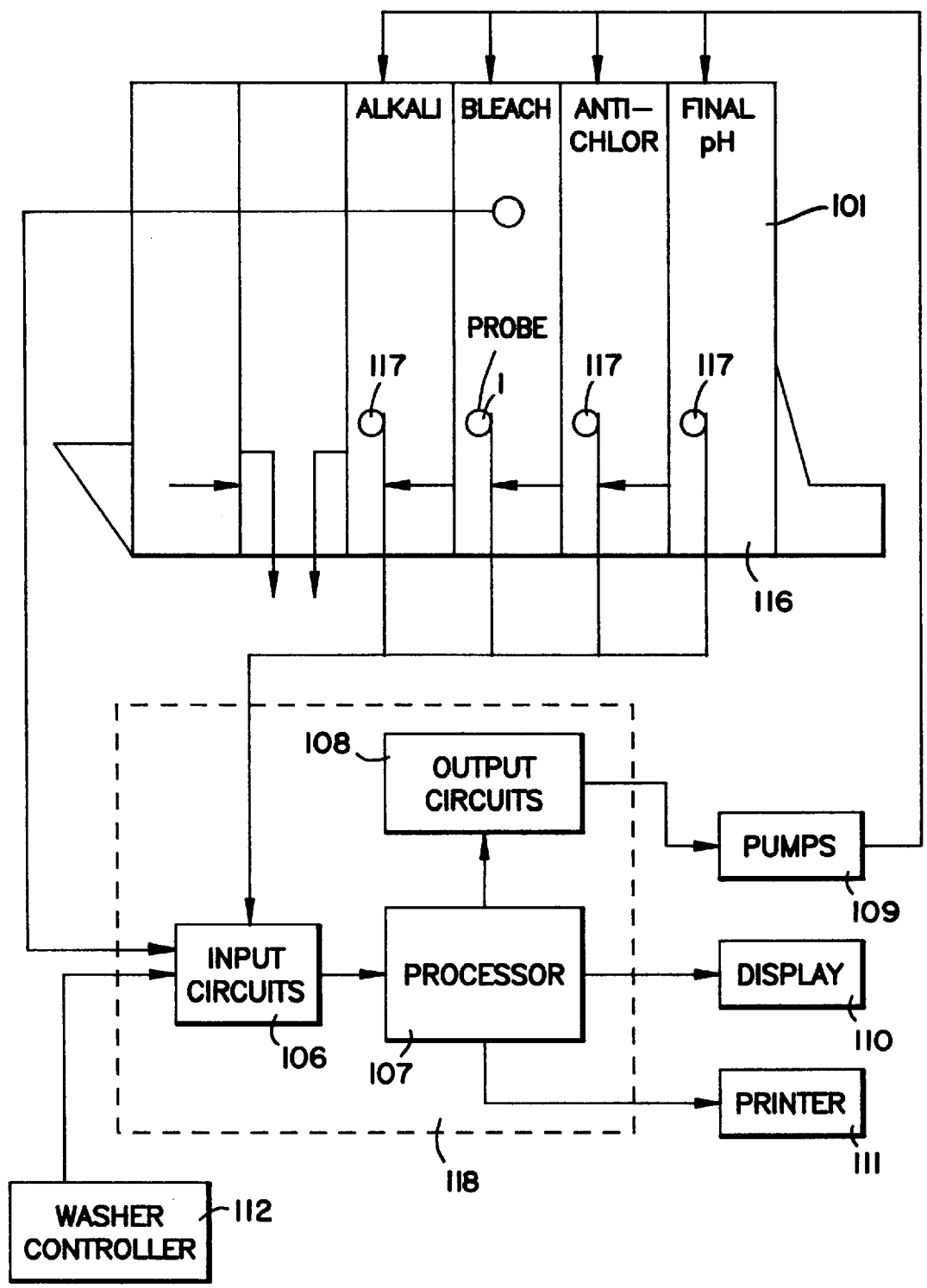
FIG. 3 is a functional block diagram which generally depicts an amperometric probe 1 utilized in an industrial laundry cleaning system 100 with feedback control for the addition of bleach.

A preferred embodiment of the amperometric probe 1 of the present invention includes the incorporation of the probe 1 in an industrial cleaning system 100 in which the probe 1 is used to measure the concentration of hypochlorite ion at pH's greater than about 10, followed by feedback control to add additional hypochlorite ion in the form of bleach to the overall process, as needed. Referring now to FIG. 3, a general schematic diagram of an overall system 100 incorporating the amperometric probe 1 of the present invention in a feed-forward bleach-addition system is depicted.

The washer system 101 includes several zones in which various environments exist. In FIG. 3, for example, Alkaline 114, Bleach 105, Anti-Chlor 115, and Final pH 116 zones are illustrated. It will be appreciated by those skilled in the art that residual bleach in the fabric may cause damage. Therefore, an anti-chlorine (Anti-Chlor) zone 115 is established with an appropriate reducing agent such as sodium metabisulfite or sodium thiosulfate to neutralize the bleach. In view of the preferred function of the anti-chlorine zone 115, it will be appreciated that the probe 1 may also be utilized in this zone. Various probes and sensors 1, 117 and 113 are included in the zones to monitor temperature and other conditions. A controller 118 for monitoring and controlling the addition of chemicals to the wash cycle includes a microprocessor 107 and attendant input circuits 106 and output circuits 108. To monitor the status of processor 107 a display 110, printer 111, and keypad (not shown) are included. A washer controller 112 (connected to the controller 118) provides washer system 101 status and/or instructions. The output circuits 108 are connected to pumps 109 which control the addition of various chemicals into the laundry system 101 zones. Those skilled in the art will appreciate that valves, gravity feed devices, etc. may also be operated by the output signals of controller 118. Temperature probe 113 (discussed below) is also illustrated.

The amperometric probe 1 is mounted within the bleach environment 105 of the washing system 101. The output signal of the probe 1 is a current signal proportional to the OCl⁻ concentration. The output signal is provided to input circuits block 106. At block 106, the signal is converted to a proportional voltage signal and amplified. This converted, amplified signal is then provided to an analog-to-digital converter. The resulting digitized signal is transmitted to processor 107 which utilizes the relative input signal to compare the actual concentration to a set point. An error value is thereby determined. If the error value indicates that the concentration has fallen below the set point, then an output signal is fed to output circuits block 108. The output circuits block 108 control the addition of bleach to the industrial washer system 101 based on a pre-set concentration which optimizes the use of chemical while providing sufficient cleansing action. Alternatively, the output circuit 108 can control a valve in order to deliver bleach in a controlled manner. A controller 118 which may be utilized is manufactured by Ecolab of St. Paul, Minn., having model designation CLS 200. However, those skilled in the art will appreciate that other controllers may be used, and the foregoing example is illustrative only.

Therefore, in operation, the probe 1 acts as a sensor in a closed loop, bleach controlling, dispensing system. If the input value is lower than the set value, a pump 109 is turned on to inject product until the actual concentration value reaches the set value. If the input value is higher than the set value, no product is injected until the value falls below the set point.

The industrial washer system 101 of FIG. 3 is one embodiment of the present invention, although it is believed such feed-back control could be used in other systems which require accurate control of bleach addition. For example, Applicants believe such systems could be used in either single use or re-use clean-in-place systems for cleaning equipment in the food industry, such as the system sold by the Food and Beverage Division of Ecolab Inc. (the assignee of the present invention) for use in cleaning equipment on dairy farms.

The amperometric probe 1 of the present invention is arranged and configured to produce an electrical output signal in proportion to the concentration of bleach in the bleach environment within which the membrane 12 surface is exposed. The operation of such amperometric solids is well-documented by Gealt in U.S. Pat. No. 3,510,421; Porter et al., U.S. Pat. No. 3,577,332; and Porter, U.S. Pat. No. 3,929,603; each of which have been incorporated by reference above.

The following examples are intended to be illustrative of the invention. However, these examples should not be construed or interpreted to otherwise limit the invention.

EXAMPLE 1

Several membranes were tested to determine which allowed maximum response to bleach at pH's of greater than about 10.

The general procedure utilized in each test included:
a. Placing 250 mL of deionized water adjusted to pH 10.5 with NaOH in a 400 mL beaker.
b. Adding an aliquot of an ≈8% NaOCl stock solution by Eppendorf pipette. [OCl$^-$] was determined by:

$$[OCl^-]_{test} = \frac{(\text{ppm OCl}^- \text{ in stock solution})(\text{aliquot volume}, \mu L)}{250,000\ \mu L}$$

The stock solution used in this work was 7.6% NaOCl.
c. Placing the probe in the beaker. Establishing a potential between anode and cathode at 0.0 V using an IBM Instruments EC225 voltammetric analyzer (data with the teflon membrane in place were obtained at −0.2 V; the measured current at any given [OCl$^-$] would be considerably less at 0.0 V).
d. After three minutes, measuring the current.

In each of these tests the applied potential was held at 0.0 volts and the current was measured, which increased linearly with increasing bleach concentration in the range of interest, 0–250 parts per million. The results of these tests are plotted in FIG. 4 for various membrane materials. As can be seen, in a preferred embodiment a PVC/acrylic membrane from Gelman Sciences No. 64501 with a diameter of 25 mm and a mean pore size of 0.8 μm provided nearly twice the response of the other membrane materials. This experiment demonstrates the direct measurement capability of the sensor and its superiority to other membranes such as that commercially available on the Model 450 probe manufactured by Rosemount Inc. of Eden Prairie, Minn., which is graphically depicted on FIG. 4.

EXAMPLE 2

Experiments were conducted to test the effects of changes in pH and temperature on the amperometric probe's ability to measure actual bleach concentration when such variable is changed.

TABLE 1

| OCL- | pH | T (F.) | Measured Current |
|---|---|---|---|
| 50.00 | 10.00 | 120.00 | −45 |
| 250.00 | 10.00 | 120.00 | −225 |
| 150.00 | 10.75 | 120.00 | −145 |
| 50.00 | 11.50 | 120.00 | −48 |
| 250.00 | 11.50 | 120.00 | −230 |
| 150.00 | 10.75 | 150.00 | −181 |
| 50.00 | 10.75 | 150.00 | −61 |
| 150.00 | 10.75 | 150.00 | −187 |
| 250.00 | 10.75 | 150.00 | −311 |
| 150.00 | 10.00 | 150.00 | −178 |
| 150.00 | 11.50 | 150.00 | −186 |
| 150.00 | 10.75 | 150.00 | −179 |
| 50.00 | 10.00 | 180.00 | −79 |
| 250.00 | 10.00 | 180.00 | −392 |
| 150.00 | 10.75 | 180.00 | −223 |
| 50.00 | 11.50 | 180.00 | −75 |
| 250.00 | 11.50 | 180.00 | −390 |
| 150.00 | 10.75 | 150.00 | −195 |

The results of Table 1 indicate that the variation of pH has very little effect on the probe 1 output. Thus, the difficulties associated with redox potential probes are overcome. The results illustrate that temperature appears to introduce a certain variation. However, temperature compensation can be easily added by merely monitoring the temperature of the bleach environment 105 (best seen in FIG. 3) with a temperature probe 113. The processor 107 can then correct for temperature variations through use of an equation or look-up table as will be appreciated by those skilled in the art.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An amperometric probe for measuring the concentration of an active bleach constituent, said probe comprising:
   a) an electrically nonconductive body defining a void for containing an electrolyte therein, and defining an opening to provide a passageway between said void and the exterior of said body;
   b) a first electrode positioned within said reservoir and in contact with the electrolyte filling said reservoir;
   c) mounting means for mounting a second electrode proximate said opening and being electrically coupled with the first electrode through the electrolyte; and
   d) a hydrophilic alkali-resistant membrane overlying said second electrode and in contact with the constituent, wherein the amperometric probe is highly selective to fluctuations in bleach concentration in an aqueous medium at pH greater than about 10.

2. The amperometric probe of claim 1, wherein said hydrophilic alkali-resistant membrane allows diffusion of hypochlorite ions and minimizes diffusion of other chemicals.

3. The amperometric probe of claim 1, wherein the hydrophilic alkali-resistant membrane is a highly porous thin cast mechanically stable polymeric film.

4. The amperometric probe of claim 1, wherein the hydrophilic alkali-resistant membrane is manufactured from a porous inorganic material.

5. The amperometric probe of claim 1, wherein said membrane is manufactured from a material selected from the group consisting of hydrophilic polysulfones, modified polysulfones, acrylics, polyamides, polyvinylidene fluorides, vinyl/acrylic copolymers and porous inorganic materials, and wherein said membrane overlays said second electrode, and is in contact with said constituent, wherein the amperometric probe is highly selective to OCl$^-$ concentration.

6. The amperometric probe of claim 1, wherein said body is an elongated cylinder having a longitudinal axis, and wherein said mounting means includes a shaft cooperatively connected to said body and arranged and configured to lie along said longitudinal axis.

7. The amperometric probe of claim 6, wherein said first electrode includes a wire wound about said shaft and the winding includes a central axis which is generally colinear with said longitudinal axis.

8. The amperometric probe of claim 6, wherein said second electrode is cooperatively mounted on said second end of said shaft.

9. The amperometric probe of claim 8, further comprising:
   a) a membrane cover arranged and configured to reside within said opening, said membrane cover including a mounting flange for connecting to said body and for providing a mating surface;
   b) porous plug means for forming a reference junction between said first and second electrodes, wherein said porous plug is arranged and configured to operatively engage said mating surface of said mounting flange;
   c) a spacer collar for fixing said second electrode spatially within said porous plug, and proximate said membrane; and
   d) wherein said porous plug, said spacer collar and said second electrode form a generally planar surface which is parallel to said membrane and which is in operative proximity to said membrane.

10. The amperometric probe of claim 9, further comprising a fill plug and a pressure relief device which are located within a second opening formed in said body, wherein the introduction of electrolyte during operation is facilitated and the internal pressure of the electrolyte is controlled.

11. An apparatus for controlling the active bleach concentration in a bleach environment of a laundry or other industrial cleaning system which comprises:
   (a) an amperometric probe for measuring the concentration of an active bleach constituent in an aqueous medium at a pH greater than about 10, said probe constructed and arranged to produce an electrical output signal in proportion to the concentration of bleach in said bleach environment;
   (b) means for measuring the electrical output signal from said amperometric probe;
   (c) means for processing the measured electrical output signal constructed and arranged to produce a proportional output signal relative to the measured electrical output signal; and
   (d) means for adding bleach to said bleach environment constructed and arranged to receive said proportional output signal and adjust the flow of bleach to said bleach environment relative to said proportional output signal.

12. The apparatus of claim 11, wherein the active bleaching source in a bleach environment is a mixture of a peracid and hydrogen peroxide.

13. The apparatus of claim 12, wherein the peracid is peracetic acid.

14. The apparatus of claim 11, wherein the active bleaching source in a bleach environment is hypochlorite ion.

15. The apparatus of claim 11 wherein the amperometric probe comprises an electrically non-conductive body with an electrolytic reservoir therein, said electrolytic reservoir containing an electrolyte, a pair of spaced electrodes, a first of said electrodes being positioned within said reservoir in contact with the electrolyte filling said reservoir, an opening defined in said body to provide a passageway between said reservoir and the exterior of said body, means for mounting a second of said electrodes on the exterior of the reservoir within the perimeter of said opening and being electrically coupled with the first electrode through the electrolyte.

16. The apparatus of claim 15 wherein a membrane manufactured from a material selected from the group consisting of hydrophilic polysulfones, modified polysulfones, acrylics, polyamites, polyvinylidene fluorides, vinyl/acrylic copolymers and porous inorganic materials and wherein said membrane overlays said second electrode and is in contact with the bleach environment.

17. The apparatus of claim 15 wherein a hydrophilic alkali-resistant membrane overlays said second electrode and is in contact with the bleach environment.

18. The apparatus of claim 11 wherein the means for adding bleach to said bleach environment comprises a reservoir containing bleach and a pump including fluid communication means and a control valve which receives the proportional output signal to adjust the flow of bleach to said bleach environment.

19. A process for controlling the active bleach concentration in a bleach environment of a laundry or other industrial cleaning system in real-time, said process including the steps of:
   (a) providing an amperometric probe for measuring the concentration of an active bleach constituent in an aqueous medium, said amperometric probe including a cathode, at which reduction of the active bleach species occurs, covered by a polymeric membrane material selected from the group consisting of hydrophilic polysulfones, modified polysulfones, acrylics, polyamides, polyvinylidene fluorides, vinyl/acrylic copolymers and porous inorganic materials, said amperometric probe mounted in a position exposing the cathode covered by the polymeric membrane material to the bleach environment;
   (b) measuring the electrical output signal from said amperometric probe;
   (c) processing the measured electrical output signal to produce a proportional output signal relative to the measured electrical output signal; and
   (d) adding bleach to said bleach environmental relative to said proportional output signal.

20. The process of claim 19, wherein the active bleach in a bleach environment is a mixture of a peracid and hydrogen peroxide.

21. The process of claim 20, wherein the peracid is peracetic acid.

22. The process of claim 19, wherein the active bleach in a bleach environment is hypochlorite ion.

* * * * *